United States Patent

Rovati et al.

[11] Patent Number: 5,204,365
[45] Date of Patent: Apr. 20, 1993

[54] SUBSTITUTED DIPHENYLMETHANE DERIVATIVES AS ANALGESIC OR ANTI-INFLAMMATORY AGENTS

[75] Inventors: Romeo A. Rovati; Ernesto F. Felip; Ricardo C. Mestres; Eduardo C. Bau, all of Barcelona, Spain

[73] Assignee: Sociedad Espanola de Especialidades Farmaco-Terapeuticas S.A., Spain

[21] Appl. No.: 705,400

[22] Filed: May 24, 1991

[30] Foreign Application Priority Data

May 25, 1990 [ES] Spain ................................. 9001460
Jul. 25, 1990 [ES] Spain ................................. 9001999

[51] Int. Cl.$^5$ ................... A61K 31/415; C07D 233/56
[52] U.S. Cl. ................................. 514/399; 548/344.1
[58] Field of Search ........................ 548/345; 514/399

[56] References Cited

FOREIGN PATENT DOCUMENTS 0146064 6/1985 European Pat. Off. .
0003796 5/1987 European Pat. Off. .
0222205 5/1987 European Pat. Off. .
0276583 8/1988 European Pat. Off. .
49-93379 9/1974 Japan .

OTHER PUBLICATIONS

Chemical Abstracts, vol. 82, No. 23, Jun. 9, 1975; Columbus, Ohio, US; Abstract No. 156367D, Nakanishi, et al., "Piperazine Derivatives", p. 618; column 1.

Primary Examiner—David B. Springer
Assistant Examiner—Lenora Ava Miltenberger
Attorney, Agent, or Firm—Trask, Britt & Rossa

[57] ABSTRACT

A compound of formula I or a pharmaceutically acceptable salt thereof

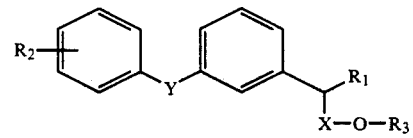

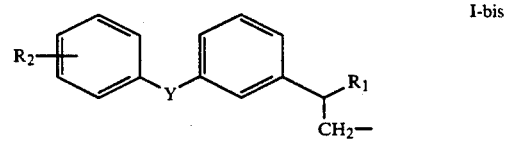

where
—$R_1$ is hydrogen or methyl;
—$X$— is —CO— or —$CH_2$—;
—$Y$— is >CH—A or its vinylogous group >C=CH—$CH_2$—A, wherein —A is a —$NR_4R_5$ group, where each $R_4$ and $R_5$, equal or different between them, is $C_1$–$C_4$-alkyl or a phenyl-substituted $C_1$–$C_4$-alkyl; or —A is the N-radical of a 5- or 6-membered, uncharged (i.e. neither quaternary nor zwitterionic) monocyclic ring, either aromatic or non-aromatic, said ring containing one N atom, two N atoms, three N atoms or an N/O pair of atoms, all other atoms in the ring being carbon, and said ring being optionally mono- or di-substituted by groups selected from $C_1$–$C_4$-alkyl, benzyl, 2-furanylmethyl and 2-thienylmethyl;
—$R_2$ is hydrogen or a radical $C_1$–$C_4$-alkyl, $C_1$–$C_4$-alkoxy, di-($C_1$–$C_4$-alkyl)amino, nitro or halogen, said radical being attached at the 2, 3 or 4 substitution positions of the phenyl ring;
—$R_3$ is hydrogen, phenyl, $C_1$–$C_{10}$-alkyl, a $C_3$–$C_{10}$-alkenyl or alkynyl group with the double or triple bond non-adjacent to the O—C bond, —$(CH_2CH_2O)_n$—H with n=1, 2 or 3, —$(CHOH)_m$—H with m=2, 3 or 4, or —when X is CO— the radical I-bis where Y is defined as above-useful as analgesic or anti-inflammatory agents.

8 Claims, No Drawings

SUBSTITUTED DIPHENYLMETHANE DERIVATIVES AS ANALGESIC OR ANTI-INFLAMMATORY AGENTS

This invention refers to new substituted diphenylmethane derivatives, their pharmaceutical compositions, their preparation process and their use as analgesic or anti-inflammatory agents without ulcerogenic side-effects.

BACKGROUND ART

The analgesic or anti-inflammatory properties of 2-(3-benzoylphenyl)propionic acid or ketoprofen, disclosed in U.S. Pat. No. 3,641,127 and structurally related to the title compounds, is well known in the art. However, it is also true that ketoprofen, as well as other commercial non-steroid analgesic or anti-inflammatory agents, such as suprofen or tiaprofenic acid, have important ulcerogenic side-effects or cause gastrointestinal harm or discomfort. Thus, the provision of analgesic or anti-inflammatory agents with lower ulcerogenic side-effects constitutes an important problem in modern therapy. Of course, such agents would be even more interesting if, on top of that, they presented some anti-ulcer activity

DISCLOSURE OF THE INVENTION

The present invention provides new substituted diphenylmethane derivatives of formula I and pharmaceutically acceptable salts thereof, useful as analgesic or anti-inflammatory agents, as proved in several analgesic/anti-inflammatory activity tests. Have the advantage of the absence of ulcerogenic side-effects (at the highest tested doses) and, in some cases, with the extra advantage of the presence of anti-ulcer activity, as proved in anti-ulcer activity tests.

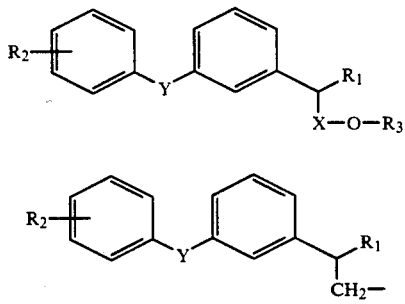

In formula I,
—$R_1$ is hydrogen or methyl;
—X— is —CO— or —$CH_2$—;
—Y— is >CH—A or its vinylogous group >C=CH—$CH_2$—A, wherein —A is a —$NR_4R_5$ group, where each $R_4$ and $R_5$, equal or different between them, is $C_1$-$C_4$-alkyl or a phenyl-substituted $C_1$-$C_4$-alkyl; or —A is the N-radical of a 5- or 6-membered, uncharged (i.e, neither quaternary nor zwitterionic) monocyclic ring, either aromatic or non-aromatic, said ring containing one N atom, two N atoms, three N atoms or an N/O pair of atoms, all other atoms in the ring being carbon, and said ring being optionally mono- or di-substituted by groups selected from $C_1$-$C_4$-alkyl, benzyl, 2-furanylmethyl and 2-thienylmethyl; —$R_2$ is hydrogen or a radical $C_1$-$C_4$-alkyl, $C_1$-$C_4$-alkoxy, di-($C_1$-$C_4$-alkyl)amino, nitro or halogen, said radical being attached at the 2, 3 or 4 substitution positions of the phenyl ring;
—$R_3$ is hydrogen, phenyl, $C_1$-$C_{10}$-alkyl, a $C_3$-$C_{10}$-alkenyl or alkynyl group with the double or triple bond non-adjacent to the O—C bond, —$(CH_2CH_2O)_n$—H with n=1, 2 or 3, —$(CHOH)_m$—H with m=2, 3 or 4, or —when X is CO— the radical I-bis where Y is defined as above.

In embodiment (a) of the present invention, compounds I have X=CO. In a preferred embodiment within (a), —Y— is >CH—A. Among them, even more preferred are those in which $R_2$ is hydrogen, $C_1$-$C_4$-alkyl or $C_1$-$C_4$-alkoxy; $R_3$ is hydrogen or $C_1$-$C_4$-alkyl, and A is 1(1H)-imidazolyl or 1-piperazinyl, whose corresponding rings are optionally mono- or bi-substituted by groups selected from $C_1$-$C_4$-alkyl, benzyl, 2-furanylmethyl and 2-thienylmethyl. The most preferred ones among this group are those in which A is 1(1H)-imidazolyl. In other preferred embodiment within (a), compounds I are those in which —Y— is >C=CH—$CH_2$—A. Among them, even more preferred are those in which $R_2$ is hydrogen, $C_1$-$C_4$-alkyl or $C_1$-$C_4$-alkoxy; $R_3$ is hydrogen or $C_1$-$C_4$-alkyl, and A is 1(1H)-imidazolyl or 1-piperazinyl, whose corresponding rings are optionally mono- or bi-substituted by groups selected from $C_1$-$C_4$-alkyl, benzyl, 2-furanylmethyl and 2-thienylmethyl. The most preferred ones among this group are those in which A is 1(1H)-imidazolyl.

In an embodiment (b) of the present invention, compounds I have X=$CH_2$. In a preferred embodiment within (b), compounds I are those in which —Y— is >CH—A. Among them, even more preferred are those in which $R_2$ is hydrogen, $C_1$-$C_4$-alkyl or $C_1$-$C_4$-alkoxy; $R_3$ is hydrogen or $C_1$-$C_4$-alkyl, and A is 1(1H)-imidazolyl or 1-piperazinyl, whose corresponding rings are optionally mono- or bi-substituted by groups selected from $C_1$-$C_4$-alkyl, benzyl, 2-furanylmethyl and 2-thienylmethyl. The most preferred ones among this group are those in which A is 1(1H)-imidazolyl. In other preferred embodiment within (b), compounds I are those in which —Y— is >C=CH—$CH_2$—A. Among them, even more preferred are those in which $R_2$ is hydrogen, $C_1$-$C_4$-alkyl or $C_1$-$C_4$-alkoxy; $R_3$ is hydrogen or $C_1$-$C_4$-alkyl, and A is 1(1H)-imidazolyl or 1-piperazinyl, whose corresponding rings are optionally mono- or bi-substituted by groups selected from $C_1$-$C_4$-alkyl, benzyl, 2-furanylmethyl and 2-thienylmethyl. The most preferred ones among this group are those in which A is 1(1H)-imidazolyl.

The preferred acid salts of compounds I are dimaleate, mono- and dihydrochloride, and they are prepared by treatment with maleic acid and hydrochloric acid, respectively. When $R_3$=H, the preferred base salts of compounds I are those with coline, lysine and phenylalanine, prepared by the conventional methods well known in the art.

Compounds I have at least two stereogenic centres, namely, two chiral centres when —Y—is >CH—A, and one chiral centre and a stereogenic double bond when —Y— is its vinylogous group, >C=CH—$CH_2$—A. Thus, compounds I have stereoisomers, both enantiomers and diasteromers. The present invention embraces all stereoisomers of I as well as their mixtures. The accompanying examples do not illustrate any separation of racemic mixtures, but in some cases they illustrate that the prepared products are mixtures of the two possible diasteromers in a ratio of substantially 1:1.

Subject matter of the present invention are also analgesic or anti-inflammatory pharmaceutical compositions for human or animal use which comprise a therapeutically effective amount of a compound I, or a therapeutically acceptable salt thereof, in combination with a pharmaceutically acceptable excipient or carrier. Subject matter of the present invention is also the use of a compound I, or a pharmaceutically acceptable salt thereof, in the preparation of a medicament for treating pain or inflammation in humans or animals.

Pharmaceutically acceptable salts are those with physiologically tolerated inorganic or organic acid or bases, such as the salts of hydrochloric acid, nitric acid, sulfuric acid, phosphoric acid, sulphonic acids and carboxylic or hydroxycarboxylic acids (such as acetic, tartaric, maleic, salicylic, citric or ascorbic acids). The preferred acid salts of compounds I are dimaleate, mono- and dihydrochloride, prepared by treatment with maleic acid and hydrochloric acid, respectively. When $R_3$=H, the preferred base salts of compounds I are those with coline, lysine and phenylalanine, prepared by the conventional methods well known in the art.

Among the pharmaceutically acceptable excipient or carriers are those solid, semi-solid and liquid diluents, as well as any other auxiliary compound, commonly used to prepare appropriate galenic formulations, such as tablets, pills, capsules, granules, solutions, suspensions, emulsions, suppositories, pastes, ointments, gels, creams, lotions, powders or sprays.

Subject matter of the present invention is also a process for the preparation of compounds of formula I, or a pharmaceutically acceptable salt thereof, comprising the following:

a) A compound of formula II

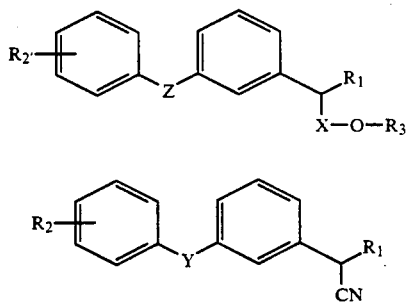

where —Z— is >CH—L when —Y— is >CH—A, or —Z— is >C=CH—CH$_2$—L when —Y— is >C=CH—CH$_2$—A, —L being a leaving group such as halogen or substituted-sulfonyloxy, is treated with H—A (for instance, a substituted 1H—imidazole or a substituted piperazine) or an equivalent nucleophilic reagent thereof (such as the trimetylsilyl derivative), in an inert solvent and in the presence of a base; then, when a given salt of I is wished, the corresponding acid or salt is added or an appropriate ionic exchange is carried out; alternatively, compounds I with X=CO are prepared from nitriles III, by simple hydrolysis when $R_3$=H, or by hydrolysis and esterification with $R_3$OH (preferably in one-pot reaction) when $R_3$ is different from H.

b) Alternatively, compounds of formula I are prepared by mutual interconversion in the following way: When X is CO, compounds I with $R_3$=H are prepared by acid or base hydrolysis from compounds I with $R_3$ different from H; complementary, compounds I with $R_3$ different from H are prepared from compounds I with $R_3$=H by esterification with an alcohol $R_3$—OH or by reaction of the acid chloride or a suitable symmetrical or mixed anhydride with $R_3$—OH, or by any other standard method of ester preparation; a compound I with $R_3$ different from hydrogen is also obtained from another compound I by transesterification, preferably if the alcohol $R_3$—OH of the starting compound has a boiling-point lower than the alcohol $R_3$—OH of the end product; when X is CH$_2$, compounds I with $R_3$=H are prepared from compounds I with $R_3$ different from H and X=CO, by reduction, preferably with lithium aluminum hydride; then, when a given salt of I is wished, the corresponding acid or salt is added or an appropriate ionic exchange is carried out.

In preferred embodiments of the preparation processes, the leaving group —L is a substituted-sulfonyloxy radical or halogen, preferably chlorine, the inert solvent employed is acetonitrile or dimethylformamide, and the base employed is sodium or potassium hydrogencarbonate. The preferred nucleophile for the substitution reaction is the own reagent H—A in excess.

Preparation processes of the present invention are summarized in Schemes 1 and 2, which also show the synthetic methods to prepare the starting materials II which are illustrated in the examples. Scheme 1 shows the preparation of compounds I when —Y— is >CH—A, whereas Scheme 2 does it when —Y— is >C=CH—CH$_2$—A. Starting materials IIa, IIb and IIc in Schemes 1 and 2 are the preferred embodiments of compound II in which the leaving group —L is chlorine and $R_3$ is H or CH$_3$. By treatment with SOCl$_2$, chlorides IIa, IIb and IIc are obtained from the corresponding alcohols IVa, IVb and IVc; these, in turn, are obtained by reduction (preferably with NaBH$_4$)of the corresponding carbonyl compounds Va, Vb and Vc. Ketone/ester Vc is obtained from the corresponding ketone/carboxylic acid VI by direct esterification. Aldehyde/ester Vb is obtained from the corresponding aldehyde/carboxylic acid Va which, in turn, is obtained from intermediate X via a Meyer-Schuster rearrangement. Intermediate X is obtained from the above-mentioned ketone/carboxylic acid VI. The above-disclosed mutual interconversions among end products I are also illustrated in Schemes 1 and 2. The accompanying examples illustrate most reactions of Schemes 1 and 2 in specific cases.

As shown in Scheme 1, A-substituted nitriles III are prepared from the corresponding nitrile/chlorides VII which, in turn, are prepared from nitrile/alcohols VIII, reduction products of nitrile/ketones XI. These nitrile/ketones can be prepared by well known methods of benzene chemistry (Friedel-Crafts acylation, Grignard reactions, rearrangements, etc), to be selected depending on the nature and position of the R$_2$ group. Scheme 3 shows three methods which have been used to prepare the nitrile/ketones IX illustrated in the examples. Method B is also suitable for the 2—R$_2$— substituted compounds.

Scheme 1:
Preparation of compounds I when —Y— is >CH—A
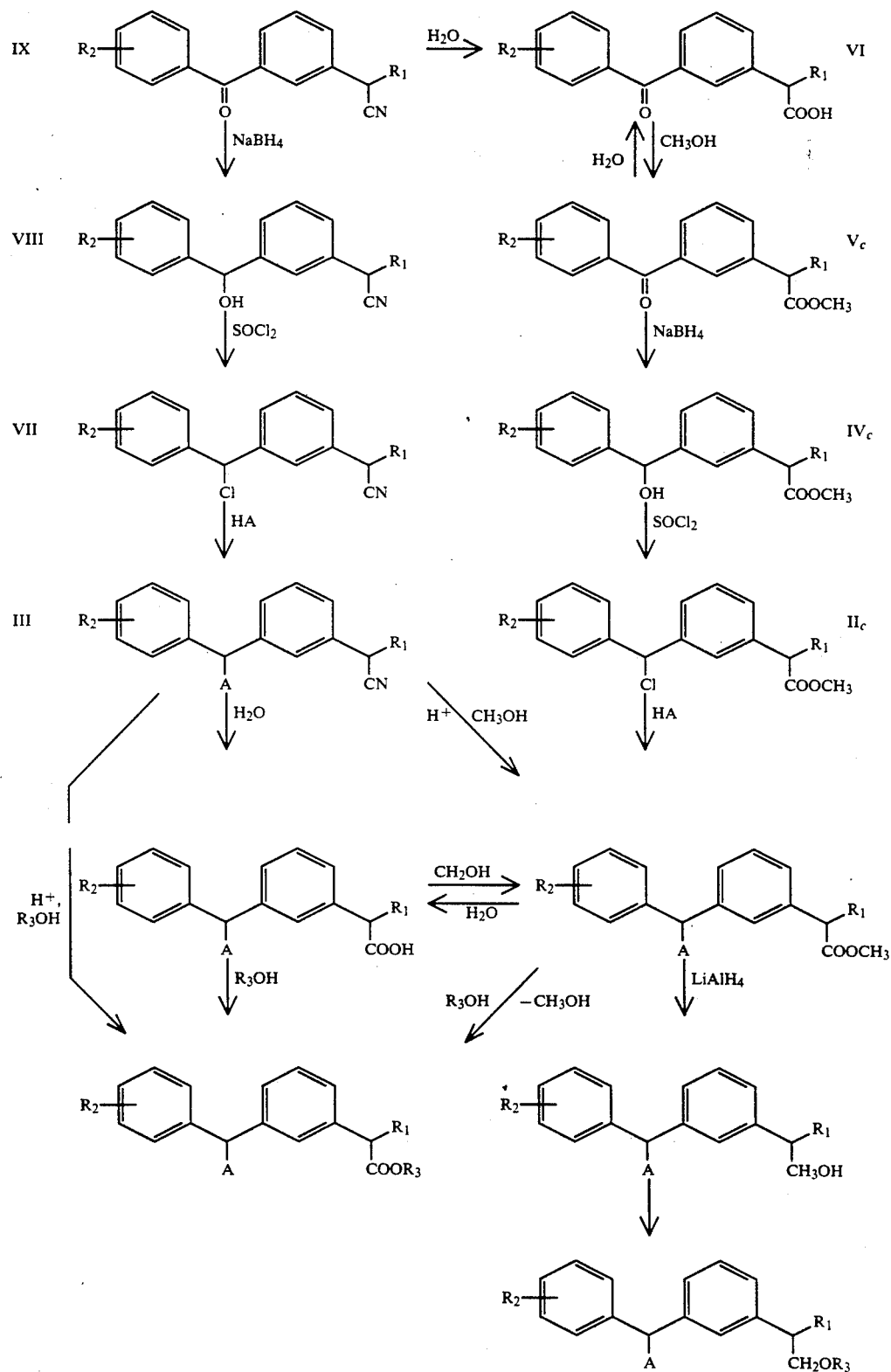

Scheme 2:
Preparation of compounds I when —Y— is >C=CH—CH₂—A
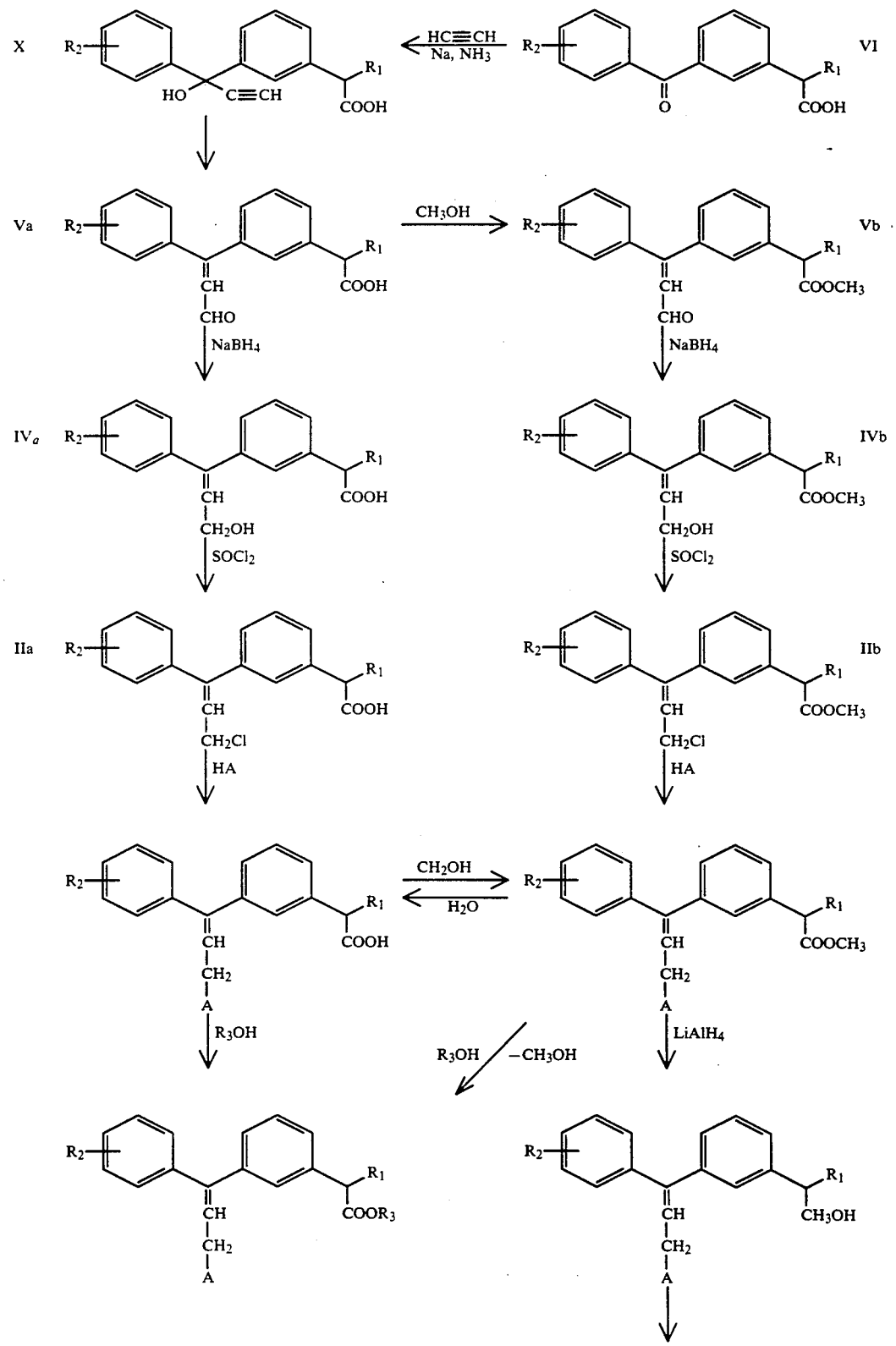

-continued

Scheme 2:

Preparation of compounds I when —Y— is $\rangle$C=CH—CH$_2$—A

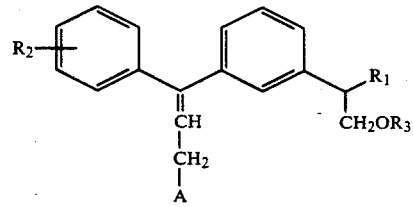

REFERENCE EXAMPLE 1

Methyl 2-(3-benzoylphenyl)propionate (Vc with $R_1$=CH$_3$ and $R_2$=H)

In a reaction flask with mechanical stirring and reflux condenser, 263 g of 2-(3-benzoylphenyl)propionic acid (VI with $R_1$=CH$_3$ and $R_2$=H) were suspended in 1L of dry benzene. Then 154 g of thionyl chloride were added and the mixture was heated under reflux for 5 hours. After cooling at room temperature, benzene and unreacted thionyl chloride were eliminated under vacuum. To the resulting residue (corresponding to the acid chloride) 400 mL of absolute methanol were added with care. The resulting solution was heated under reflux for 5 hours. After cooling at room temperature, the solvent was eliminated under vacuum and the residue was dissolved in 250 mL methylene chloride. The solution was washed and neutralized by treating it three times with 200 mL of a 5% solution of sodium hydrogencarbonate and then with water. After being dried, the solvent was evaporated under vacuum and 256 g of an oily residue was obtained (92% yield), used without further purification in the reaction of the following example. After 24 hours of drying, a white solid of m.p. 50-2° C. was obtained. After recrystalization from cyclohexane, experimental m.p. was 51-2° C. and the solid was identified as the title compound. By following analogous procedures, compounds Vc of Table 1 were prepared.

TABLE 1

| | | Compounds Vc |
|---|---|---|
| $R_1$ | $R_2$ | Identification data (IR in cm$^{-1}$, film) |
| CH$_3$ | H | white solid; m.p. 51-2° C. |
| CH$_3$ | 4-CH$_3$ | colourless oil; IR: 3110-2820, 1740, 1660, 1440, 1280, 1210, 1170, 1070, 945 |
| CH$_3$ | 4-Cl | yellow solid; m.p. 63-5° C. |
| CH$_3$ | 4-OCH$_3$ | yellow oil; IR: 3090-2820, 1740, 1655, 1600, 1260, 1170, 1030, 845, 760, 710. |
| CH$_3$ | 4-N(CH$_3$)$_2$ | oil; IR: 3100-2820, 1735, 1640, 1595, 1370, 1320, 1175, 940, 830, 760. |
| CH$_3$ | 4-F | yellow solid; m.p. 36-7° C. |
| CH$_3$ | 3-Cl | white solid; m.p. 72-3° C. |

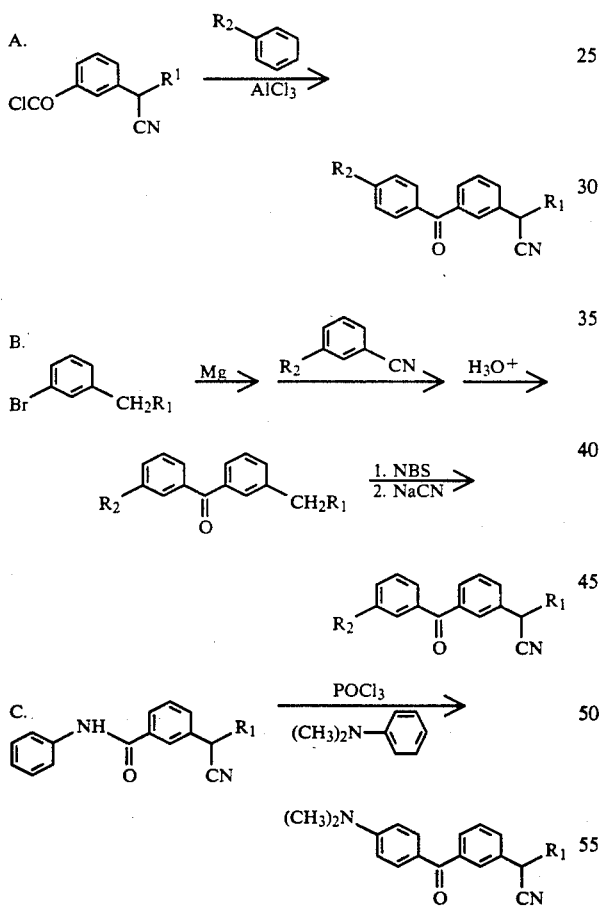

Scheme 3:
Some preparative methods for nitrile/ketones (IX), used as starting materials.

Specially preferred embodiments of the present invention are the specific compounds I included in the accompanying Tables 6 and 7 of the Examples. According to the present invention, compounds of formula I are useful as analgesic or anti-inflammatory agents, with the advantage of the absence of ulcerogenic side-effects (at the highest tested doses) and, in some cases, with the extra advantage of the presence of anti-ulcer activity, as proved in several analgesic/anti-inflammatory and anti-ulcer tests.

REFERENCE EXAMPLE 2

Methyl 2-[3-(phenylhydroxymethyl)phenyl]propionate (IVc with $R_1$=CH$_3$ and $R_2$=H)

To a solution of 164 g of methyl 2-(3-benzoylphenyl)-propionate in 1100 mL methanol at a 0° C., 14 of sodium borohydride were added, keeping the temperature between 7 and 10° C. After 2 hours of stirring at 0° C., TLC (silica-gel/chloroform) showed total consumption of starting material. The solvent was evaporated under vacuum. The residue was dissolved in 400 mL of methylene chloride. The solution was washed three times with 250 ml of 1% hydrochloric acid, until acid pH, and then with saturated sodium chloride solution, until neutral pH. After evaporation of the solvent, the oily colourless residue wheighted 160,0 g (97% yield) and was identified as the title compound. IR Spectrum (film), cm$^{-1}$: 3480 (broad), 3080-2880, 1730, 1455, 1200, 1175, 1110, 700. In the 200 MHz $^1$H-NMR apparatus the signal of CH$_3$ appears as two doublets of similar intensity, indicating the presence of the two possible diasteromers. By following analogous procedures, compounds IVc of Table 2 were obtained.

TABLE 2

| | | Compounds IVc |
|---|---|---|
| R$_1$ | R$_2$ | Identification data (IR in cm$^{-1}$, film) |
| CH$_3$ | H | colourless oil; IR: 3480 (broad), 3080-2880, 1730, 1455, 1200, 1175, 1110, 700 |
| CH$_3$ | 4-CH$_3$ | colourless oil; IR: 3480 (broad), 3090-2880, 1740, 1440, 1230, 1205, 1180, 1045, 1030, 770, 710. |
| CH$_3$ | 4-Cl | yellow oil; IR: 3480 (broad), 3080-2860, 1730, 1610, 1490, 1440, 1340, 1230, 1200, 1090, 1020, 800, 760, 710. |
| CH$_3$ | 4-OCH$_3$ | yellow oil; IR: 3490 (broad), 3080-2850, 1735, 1610, 1510, 1250, 1175, 1030, 760 |
| CH$_3$ | 4-N(CH$_3$)$_2$ | yellow oil; IR: 3500 (broad), 3100-2780, 1735, 1615, 1520, 1440, 1170, 1125, 945, 810, 700 |
| CH$_3$ | 4-F | yellow oil; IR: 3400 (broad), 3030-2820, 1710, 1585, 1490, 1200, 1135, 1015, 820 |
| CH$_3$ | 3-Cl | yellow oil; IR: 3380 (broad), 3030-2820, 1710, 1420, 1180, 1060, 1020, 770, 695. |

REFERENCE EXAMPLE 3

Methyl 2-[3-(phenylchloromethyl)phenyl]propionate (IIc with R$_1$=CH$_3$ and R$_2$=H)

Methyl 2-[3-(phenylhydroximethyl)phenyl]propionate (128 g) was dissolved in 100 mL of dry methylene chloride and the solution was cooled to 0° C. Then 41 mL of thionyl chloride in 50 mL methylene chloride were added along 1 hour, keeping the reaction temperature between 5 and 10° C. After staying for 1 hour at 5° C. and 1 hour at room temperature, solvents were removed and the residue (130.5 g, yellow oil) was vacuum distilled, yielding 103 g (75% yield) of the title compound as a yellow transparent liquid, b.p. 158-163° C./1 tor. In the 200 MHz $^1$H-NMR apparatus the signal of CH$_3$— appears as two doublets of similar intensity, indicating the presence of the two possible diasteromers. By following analogous procedures, compounds IIc of Table 3 were obtained.

TABLE 3

| | | Compounds IIc |
|---|---|---|
| R$_1$ | R$_2$ | Identification data (IR in cm$^{-1}$, film) |
| CH$_3$ | H | yelow liquid; b.p. 158-63° C./1 tor |
| CH$_3$ | 4-CH$_3$ | yellow liquid; b.p. 162-5° C./0.5 tor |
| CH$_3$ | 4-Cl | yellow oil; b.p. 173-4° C./1 tor |
| CH$_3$ | 4-OCH$_3$ | yellow oil; IR: 3090-2840, 1735, 1610, 1510, 1250, 1175, 1035, 830, 730, 700 |
| CH$_3$ | 4-N(CH$_3$)$_2$ | hydrochloride: m.p. 60-7° C. |
| CH$_3$ | 4-F | colourless oil; b.p. 145-6° C./0.2 tor |
| CH$_3$ | 3-Cl | oil; IR: 3020-2820, 1720, 1580, 1420, 1180, 1150, 1060, 770, 690. |

REFERENCE EXAMPLE 4

2-[3-(4-methylbenzoyl)phenyl]propionitrile (IX with R$_2$=4—CH$_3$, R$_1$=CH$_3$).

To a stirred suspension of 32 g of powdered AlCl$_3$ in 250 mL of toluene, 23.3 g of fresh chloride of 3-(1-cianoethyl)benzoic acid were added along 10 min. The mixture was then heated under reflux for 3 hours. After cooling at room temperature, it was poured on a mixture of 115 mL of concentrated hydrochloric acid and 700 g of ice, while strongly stirring. By extraction with ethyl ether, 29.5 g of the title compound were obtained as an oil that crystallized after some time. M.p. was 52-5° C. after recrystallization from diisopropilic ether. By following procedures analogous to this one or to those shown in Scheme 3, compounds IX of Table 4 were obtained.

TABLE 4

| | | Compounds IX |
|---|---|---|
| R$_1$ | R$_2$ | Identification data (IR in cm$^{-1}$, film) |
| CH$_3$ | 4-CH$_3$ | m.p. 52-5° C. |
| CH$_3$ | 4-Cl | yellow solid; m.p. 69-71° C. |
| CH$_3$ | 4-OCH$_3$ | white solid; m.p. 68-71° C. (solvent:S$_2$C) |
| CH$_3$ | 4-N(CH$_3$)$_2$ | yellow solid; m.p. 79-80° C. |
| CH$_3$ | 4-F | white solid; m.p. 49-51° C. |
| CH$_3$ | 3-Cl | yellow oil; b.p. 160-80° C./0.1 tor |

REFERENCE EXAMPLE 5

2-[3-(4-methylbenzoyl)phenyl]propionic acid with R$_2$=4—CH$_3$ and R$_1$=CH$_3$)

A stirred suspension of 28 g of 2-[3-(4-methylbenzoyl)phenyl]propionitrile in 265 mL of 3N aqueous sodium hydroxide was heated under reflux for 24 hours. After cooling, the solution was diluted with 500 mL of water and it was washed two times with 250 mL of ethyl ether. Concentrated hydrochloric acid was added to the aqueous phase until acid pH, and an oil separated. Two extractions with 125 mL of methylene chloride were carried out. The acid residue of the organic phase was washed out with a saturated solution of sodium chloride. The removal of the solvent yielded 27.1 g (87%) of the title compound as an oil, which crystallized after some time. By recrystallization from petroleum ether/benzene (20:6) the title compound was obtained as a white solid of m.p. 67-9° C. By following procedures analogous to this one, compounds VI of Table 5 were obtained. Compound with F was obtained by acid hydrolysis.

TABLE 5

| | | Compounds VI |
|---|---|---|
| R$_1$ | R$_2$ | Identification data (IR in cm$^{-1}$, film) |
| CH$_3$ | 4-CH$_3$ | white solid; m.p. 67-9° C. |
| CH$_3$ | 4-Cl | white solid; m.p. 137-9° C. |
| CH$_3$ | 4-OCH$_3$ | white solid; m.p. 78-82° C. |
| CH$_3$ | 4-N(CH$_3$)$_2$ | yellowish solid; m.p. 70° C. |
| CH$_3$ | 4-F | white solid; m.p. 119-20° C. |
| CH$_3$ | 3-Cl | m.p. 79-83° C. |

REFERENCE EXAMPLE 6

WAS-5603:
1-[[3-(1-methoxycarbonylethyl)phenyl]phenylmethyl]-4-(2-thienylmethyl)piperazine (I with Y phenylmethyl]-4-(2-thienylemthyl)piperazine (I with Y=>CH—A, A=1-[4-(2-thienylmethyl)piperazinyl], $R_1$=CH$_3$, $R_2$=H and $R_3$=CH$_3$)

Methyl 2-[3-(phenylchloromethyl)phenyl]propionate (IIc with $R_1$=CH$_3$ and $R_2$=H) was place stirred flask (31.7 g). Then 200 mL acetonitrile and 18 g sodium hydrogencarbonate were added. A solution of 20 g of 1-(2-thienylmethyl)piperazine, denoted H-(2-Tmp) in the following, in 100 mL of acetonitrile were added and the mixture was heated under reflux for 12 hours. After cooling and filtering out inorganic salts, the solvent was removed. The residue was dissolved in 200 mL of methylene chloride, it was then washed with water, dried and evaporated, yielding 44.0 g of a yellow oil, mixture of two diasteromes (according to the two doublets in the $^1$H-NMR 200 MHz spectrum). IR spectrum (film), cm$^{-1}$: 3100–2700, 1735, 1600, 1445, 1335, 1185, 1150, 995, 840, 700. 1-(2-Thienylmethyl)piperazine was prepared according to a method analogous to the one disclosed in Organic Synthesis 1973, Col. vol. V, p 88. By following procedures analogous to this one or to those of Schemes 1 and 2, compounds I of Tables 6 and 7 were prepared. These tables also show the corresponding company codes.

TABLE 6

Compounds I ($R_1$ = CH$_3$, $R_2$ = H and Y = >CH—A)

| WAS | code | X | A | R$_3$ | Identification data |
|---|---|---|---|---|---|
| 5626 | hc | CH$_2$ | 1-Imz | H | m.p. 160–70° C. |
| 5609 | | CO | 1-Imz | H | IR: 3500–2800, 1715, 1490, 1450, 1220, 1080, 750 |
| 5608 | hc | CO | 1-Imz | CH$_3$ | m.p. 157–9° C. |
| 5660 | hc | CO | 1-Imz | CH$_2$CH$_3$ | m.p. 125–30° C. |
| 5661 | hc | CO | 1-Imz | CH$_2$CH$_2$CH$_3$ | m.p. 104–9° C. |
| 5643 | hc | CO | 1-Imz | CH(CH$_3$)$_2$ | m.p. 60–1° C. |
| 5647 | | CO | 1-Imz | (CH$_2$CH$_2$O)$_2$—H | IR: 3300 (broad), 3040–2850, 1730, 1490, 1455, 1225, 1180, 1130, 1080, 730 |
| 5650 | | CO | 1-Imz | I-bis | IR: 3100–2900, 1730, 1490, 1450, 1250, 1220, 1075, 800 |
| 5603 | | CO | 2-Tmp | CH$_3$ | IR: 3100–2700, 1735, 1600, 1445, 1335, 1185, 1150, 995 |
| 5602 | | CO | 2-Tmp | CH$_3$ | m.p. 80–9° C. |
| 5602-dimaleate | | | | | m.p. 103–7° C. |
| 5637 | hc | CO | 1-Trz | CH$_3$ | m.p. 55–6° C. |
| 5642 | | CO | 1-Trz | CH$_3$ | m.p. 49–55° C. |
| 5644 | 2hc | CO | 1-Bpz | CH$_3$ | m.p. 80–1° C. |
| 5645 | | CO | 1-Bpz | H | m.p. 92–7° C. |

1-Imz = 1(1H)-Imidazolyl; 1-Trz = 1-(1,2,4-triazolyl);
2-Tmp = 1-[4-(2-thienylmethyl)piperazinyl];
1-Bpz = 1-(4-benzylpiperazinyl); hc = hydrochloride;

TABLE 7

Compounds I (X = CO, A = 1-Imz and $R_1$ = CH$_3$)

| WAS | code | Y | R$_2$ | R$_3$ | Identification data |
|---|---|---|---|---|---|
| 5630 | hc | >CH—A | 4-Cl | CH$_3$ | m.p. 50–1° C. |
| 5633 | | >CH—A | 4-Cl | H | m.p. 130–1° C. |
| 5631 | | >CH—A | 4-CH$_3$ | CH$_3$ | IR: 3110–2850, 1740, 1610, 1490, 1440, 1225, 1200, 1170, 1075, 905 |
| 5631 | hc | >CH—A | 4-CH$_3$ | CH$_3$ | m.p. 80–1° C. |
| 5634 | | >CH—A | 4-CH$_3$ | H | m.p. 70–3° C. |
| 5639 | hc | >CH—A | 4-OCH$_3$ | CH$_3$ | m.p. 76–7° C. |
| 5640 | | >CH—A | 4-OCH$_3$ | H | m.p. 75–6° C. |
| 5653 | 2hc | >CH—A | 4-N(CH$_3$)$_2$ | CH$_3$ | m.p. 100–10° C. |
| 5654 | hc | >CH—A | 4-F | CH$_3$ | m.p. 65–6° C. |
| 5655 | | >CH—A | 4-F | H | m.p. 70–5° C. |
| 5658 | hc | >CH—A | 3-Cl | CH$_3$ | m.p. 135–8° C. |
| 5659 | | >CH—A | 3-Cl | H | m.p. 90–6° C. |
| 5611 | hc | >C=CH—CH$_2$—A | H | H | solid; IR: 3500–2600, 1725, 1575, 1445, 1280, 1170, 1080, 750, 705 |
| 5610 | | >C=CH—CH$_2$—A | H | CH$_3$ | oil; IR: 3100–2900, 1740, 1505, 1445, 1230, 1210, 1170, 1080, 910 |

EXAMPLE 7

2-[3-(1-Phenyl-1-hydroxy-2-propinyl)phenyl]propionic acid (X with $R_2$=H and $R_1$=CH$_3$)

In a 20 reactor with mechanical stirring, thermometer and addition funnel, sodium acetylide was prepared at −70° C. (according to the method of Org. Synth. Col. Vol. IV, p. 117), by addition of 173 g of chopped sodium metal to 10 L liquid ammonia saturated of dry acetylene, which was constantly bubbled along the addition. After all the sodium was consumed, a solution of 762 g of 2-(3-benzoilphenyl)propionic acid in 1 L dry THF and 1 L dry ethyl ether was added. A white solid precipitated. The mixture was stirred for 2 hours, allowing the ammonia to evaporate. The residue was dissolved in 4 L water and 4 L ethyl ether, and this solution was brought to pH 1 by addition of 50% sulphuric acid. The aqueous phase was extracted with 3 L ethyl ether. The organic extract was washed with saturated sodium chloride and water until neutral. After removing the solvent, 840 g of an oil were obtained, identified as the title compound. IR Spectrum (film), cm$^{-1}$: 3500–2700, 3300, 1710, 1450, 1200, 1050, 1000, 700.

EXAMPLE 8

2-[3-(1-Phenyl-2-formylvinyl)phenyl]propionic acid (Va with $R_2$=H and $R_1$=$CH_3$)

A solution of 840 g of 2-[3-(1-phenyl-1-hydroxy-2-propinyl)phenyl]propionic acid in 2,5 L dioxane was added, along 20 min, to a mixture of 367,5 g of 96% sulphuric acid, 1,11 L water and 1,35 L dioxane, being kept under reflux. The reflux was kept for 15 extra minutes. Then the mixture was poured on 10 L of ice-water with strong stirring. The precipitated solid was filtered out, whashed with water and ethyl ether and dried, yielding 320 g (40% yield) of a chromatographically-pure white solid of m.p. 145,5–7° C., identified as the title compound. IR Spectrum IR, cm$^{-1}$: 3600–2600, 1735, 1640, 1210, 1140, 870, 800, 700.

EXAMPLE 9

2-[3-(1-Phenyl-3-hydroxy-1-propenyl)phenyl]propionic acid (IVa with $R_2$=H and $R_1$=$CH_3$)

A solution of 8 g sodium hydroxide in 10 mL water and 40 mL methanol was added to a mechanically-stirred suspension of 56,1 g of 2-[3-(1-phenyl-2-formylvinyl)phenyl]propionic acid in 150 mL methanol. To the resulting solution, kept at $-5°$ to $0°$ C., 9.5 g sodium borohydride were added and the mixture was stirred for 30 min. Methanol was removed under vacuum. The residue was dissolved and extracted in 150 mL water and 150 mL methylene chloride, and then it was acidified with 5% hydrochloric acid. The organic layer was washed with water until neutral, dried and evaporated, yielding 54.2 g (96% yield) of an oil identified as the title compound. IR Spectrum (film), cm$^{-1}$: 3500–2700, 1710, 1600, 1490, 1220, 1075, 1010, 755, 700.

EXAMPLE 10

2-[3-(1-Phenyl-3-chloro-1-propenyl)phenyl]propionic acid (IIa with $R_2$=H and $R_1$=$CH_3$)

A solution of 18.5 g of dry thionyl chloride in 30 mL methylene chloride was added, along 1 hour, to a solution of 41.7 g of 2-[3-(1-phenyl-3-hydroxy-1-propenyl)phenyl]propionic acid in 60 mL of the same solvent, kept at 5–10° C. After standing for 1 hour, volatile materials were removed under vacuum. The oily residue, mainly formed by the title compound, was used in subsequent reactions without further purification. IR Spectrum (film), cm$^{-1}$: 3400–2600, 1710, 1600, 1490, 1410, 1245, 1230, 1070, 790, 770, 700.

EXAMPLE 11

Methyl 2-[3-(1-phenyl-2-formylvinyl)phenyl]propionate (Vb with $R_2$=H and $R_1$=$CH_3$)

To a solution of 56 g of 2-[3-(1-phenyl-2-formilvinil)-phenyl]propionic acid in 250 mL anhydrous THF, 32.4 g N,N'-carbonyldiimidazole were added, with stirring until formation of carbon dioxide ceased. Then 10 mL anhydrous methanol was added and the mixture was heated under reflux for 3 hours. After removing volatile compounds under vacuum, the residue was dissolved in 300 mL methylene chloride, it was washed with 5% sodium hydrogencarbonate and water until neutral, it was dried and evaporated, yielding 52 g (89% yield) of the title compound as a yellowish oil. IR Spectrum (film), cm$^{-1}$: 3060–2800, 1740, 1665, 1190, 1155, 1115, 1070, 850, 690.

EXAMPLE 12

Methyl 2-[3-(1-phenyl-3-hydroxy-1-propenyl)phenyl]propionate (IVb with $R_2$=H and $R_2$=H and $R_1$=$CH_3$)

To a solution of 28 g of methyl 2-[3-(1-phenyl-2-formilvinil)phenyl]propionate in 150 mL methanol kept at 0° C., 3.6 g sodium borohydride was added portionwise. After 30 min stirring, methanol was removed under vacuum. The residue was dissolved in 150 mL water and 200 mL chloroform, and it was acidified with 5% hydrochloric acid. The organic layer was washed until neutral, dried and evaporated, yielding 26.0 g (98% yield) of the title compound as a colourless oil. IR Spectrum (film), cm$^{-1}$: 3400 (broad), 1740, 1430, 1200, 1170, 1070, 1020, 800, 700.

EXAMPLE 13

Methyl 2-[3-(1-phenyl-3-chloro-1-propenyl)phenyl]propionate (IIb with $R_2$=H and $R_1$=$CH_3$)

In a three-necked flask with thermometer and presion-compensated addition funnel, a solution of 14.0 g of methyl 2-[3-(1-phenyl-3-hydroxy-1-propenyl)phenyl]propionate in 20 mL dry methylene chloride was placed and cooled to 0° C. A solution of 3.77 mL of thionyl chloride and 5 mL methylene chloride was added along 30 min, keeping the temperature at 5–10° C. After standing for 1 hour, solvents were removed under vacuum. The resulting residue (13,8 g) was identified as the title compound and it was used in subsequent reaction without any further purification. IR Spectrum (film), cm$^{-1}$: 3080–2910, 1740, 1430, 1240, 1200, 1160, 1065, 690.

Specific embodiments of the present invention are also those set forth in the accompanying claims.

We claim:

1. A compound of the following formula:

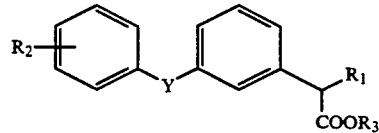

or a pharmaceutically acceptable salt thereof, where:
—$R_1$ is hydrogen or methyl;
—Y— is >CH—A or its vinylogous group >C=CH—$CH_2$—A, wherein —A is 1(1H)-imidazolyl optionally mono- or bi-substituted by a group selected from $C_1$-$C_4$-alkyl or benzyl; —$R_2$ is hydrogen or a radical $C_1$-$C_4$-alkyl, $C_1$-$C_4$-alkoxy, di($C_1$-$C_4$-alkyl)amino, nitro or halogen, said radical being attached at the 2, 3 or 4 substitution positions of the phenyl ring;
—$R_3$ is hydrogen, phenyl, $C_1$-$C_{10}$-alkyl, a $C_3$-$C_{10}$-alkenyl or alkynyl group with the double or triple bond non-adjacent to the O—C bond, $(CH_2CH_1O)_n$—H with n=1, 2 or 3, —CHOH)$_m$—H with m=2, 3 or 4.

2. A compound according to claim 1 which has the following formula:

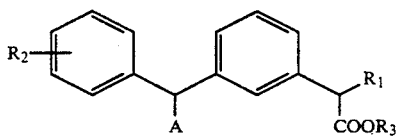

or a pharmaceutically acceptable salt thereof, where: —R$_1$, —R$_2$ —R$_3$ and —A are as defined in claim 1.

3. A compound according to claim 2 which has the following formula:

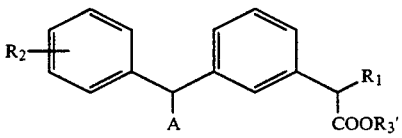

or a pharmaceutically acceptable salt thereof, where —R$_3'$ is hydrogen or C$_1$-C$_4$-alkyl, and —R$_1$, —R$_2$ and —A are as defined in claim 2.

4. A compound according to claim 3 which has the following formula:

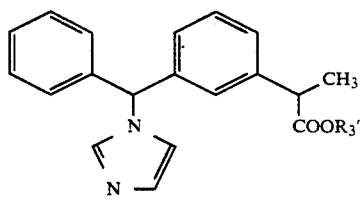

or a pharmaceutically acceptable salt thereof where —R$_3'$ is as defined in claim 3.

5. A compound according to claim 3 or 5, or a pharmaceutically acceptable salt thereof, where —R$_3'$ is methyl.

6. The dimaleate, mono or dihydrochloride salt of a compound in any one of claims 1-5.

7. An analgesic or anti-inflammatory pharmaceutical composition for human or animal use which comprises a therapeutically effective amount of a compound according to any one of claims 1-6, in combination with a pharmaceutically acceptable excipient or carrier.

8. Method of treatment of a human or animal suffering from pain or inflammation, consisting in administering to said human or animal a therapeutically effective dose of a compound as in one of claims 1-6, in combination with a pharmaceutically acceptable excipient or carrier.

* * * * *